(12) United States Patent
Piotti et al.

(10) Patent No.: US 9,207,234 B2
(45) Date of Patent: Dec. 8, 2015

(54) THERMALLY STABLE SERS TAGGANTS (75) Inventors: Marcelo Eduardo Piotti, Freemont, CA (US); Michael J. Natan, Los Altos, CA (US)

(73) Assignee: SICPA Holding SA (CH)

( * ) Notice: Subject to any disclaimer, the term of this patent is extended or adjusted under 35 U.S.C. 154(b) by 0 days.

(21) Appl. No.: 13/319,624

(22) PCT Filed: May 18, 2010

(86) PCT No.: PCT/US2010/035296
§ 371 (c)(1),
(2), (4) Date: Nov. 9, 2011

(87) PCT Pub. No.: WO2010/135351
PCT Pub. Date: Nov. 25, 2010

(65) Prior Publication Data
US 2012/0062886 A1    Mar. 15, 2012

Related U.S. Application Data

(60) Provisional application No. 61/179,281, filed on May 18, 2009, provisional application No. 61/181,598, filed on May 27, 2009.

(51) Int. Cl.
*G01J 3/44* (2006.01)
*G01N 33/532* (2006.01)
*G01N 21/65* (2006.01)
*G01N 33/28* (2006.01)

(52) U.S. Cl.
CPC ............ *G01N 33/532* (2013.01); *G01N 21/658* (2013.01); *G01N 33/28* (2013.01)

(58) Field of Classification Search
CPC .................................................... G01N 33/532
USPC ............................................................ 356/301
See application file for complete search history.

(56) References Cited

U.S. PATENT DOCUMENTS

| 2004/0191921 A1* | 9/2004 | Farquharson et al. ........ 436/172 |
| 2005/0002857 A1* | 1/2005 | Pez et al. .................... 423/648.1 |
| 2005/0056118 A1* | 3/2005 | Xia et al. ....................... 75/330 |

(Continued)

FOREIGN PATENT DOCUMENTS

WO    WO 2009/040114    5/2009

OTHER PUBLICATIONS

International Search Report and Written Opinion mailed Aug. 4, 2010 for corresponding International Patent Application No. PCT/US10/35296.

(Continued)

*Primary Examiner* — Tarifur Chowdhury
*Assistant Examiner* — Omar Nixon
(74) *Attorney, Agent, or Firm* — Swanson & Bratschun, L.L.C.

(57) ABSTRACT

An optically active particle and a method of manufacturing said particles, plus methods of tagging a material of interest with said particles are disclosed. The particle comprises a surface-enhanced spectroscopy (SES) active core and a SES active reporter associated with the SES core wherein the particle produces a measurable and thermally stable SES spectrum upon optical interrogation. As used in the disclosure, thermally stable may be defined as maintaining a measurable SES spectrum after the particle or any material tagged with the particle has been exposed to a temperature substantially higher than room temperature.

18 Claims, 2 Drawing Sheets

(56) References Cited

U.S. PATENT DOCUMENTS

| | | |
|---|---|---|
| 2005/0217424 A1* | 10/2005 | Natan .............................. 75/332 |
| 2006/0054506 A1 | 3/2006 | Natan et al. |
| 2008/0209876 A1 | 9/2008 | Miller |
| 2009/0121193 A1 | 5/2009 | Natan et al. |

OTHER PUBLICATIONS

Parlak et al., "The effect of thermal barrier coating on a turbo-charged Diesel engine performance and exergy potential of the exhaust gas", Energy Conversion and Management (2005) vol. 46, pp. 489-499.

* cited by examiner

THERMALLY STABLE SERS TAGGANTS

RELATED APPLICATIONS

This application is a 35 U.S.C. §371 national phase application of Thermally Stable SERS Taggants (WO 2010/135351), filed on May 18, 2010, entitled "Thermally Stable SERS Taggants ", which application claims the benefit of U.S. Provisional Application Ser. No. 61/181,598, filed May 27, 2009, and U.S. Provisional Application Ser. No. 61/179,281, filed May 18, 2009, which are incorporated herein by reference in its entirety.

TECHNICAL FIELD

The disclosed embodiments relate to surface enhanced spectroscopy active nanoparticles. More specifically, the disclosed particles and methods include particles with compositions or structures that provide for enhanced or increased thermal stability when compared to other spectroscopy active nanoparticles.

BACKGROUND

Certain spectroscopy techniques feature the enhancement of a spectroscopic signal through electromagnetic interaction at a surface. Representative surface enhanced spectroscopic (SES) techniques include, but are not limited to surface enhanced Raman spectroscopy (SERS) and surface enhanced resonance Raman spectroscopy (SERRS). In SERS or SERRS, a metal or other enhancing surface will couple electromagnetically to incident electromagnetic radiation and create a locally amplified electromagnetic field that leads to $10^2$- to $10^9$-fold or greater increases in the Raman scattering of a SERS active molecule situated on or near the enhancing surface. The output in a SERS experiment is the fingerprint-like Raman spectrum of the SERS active molecule.

SERS and other SES techniques can be implemented with particles such as nanoparticles. For example, gold is a SERS enhancing surface, and gold colloid may be suspended in a mixture to provide for enhanced Raman spectrum detection. SERS may also be performed with more complex SERS-active nanoparticles, for example SERS nanotags, as described in U.S. Pat. Nos. 6,514,767, 6,861,263, 7,443,489 and elsewhere. In a SERS nanotag, a reporter molecule is adsorbed to a SERS-active surface, and both the SERS-active surface and the reporter are encapsulated, typically with silica or another relatively impervious material. One advantage of a silica or glass coating is that it prevents the adsorbed molecule from diffusing away. The coating or shell also prevents other molecules from adsorbing to the enhancing surface or particle core. This configuration imparts a level of robustness and environmental insensitivity to the particles that is, for many applications, a desirable feature.

Environmental insensitivity and robustness will cause a SERS nanotag to be spectroscopically static. In many implementations, it is desirable that a SERS nanotag returns the same signal virtually no matter how long the tag has been applied to an item or embedded in a substance and no matter how many types of compound or solution are contacted with the SERS nanotag. It is also desirable, but problematic, that a SERS nanotag or similar taggant be relatively insensitive to temperature fluctuations. In particular, it is desirable that the signal capacity of taggants used to mark substances or items that are subjected to elevated temperatures not degrade as a function of elevated temperature. This is problematic in the case of SERS nanotags as described in U.S. Pat. Nos. 6,514,767, 6,861,263, 7,443,489 and elsewhere because the organic reporter molecules described therein can degrade and lose SERS activity at certain elevated temperatures.

Figure 1:
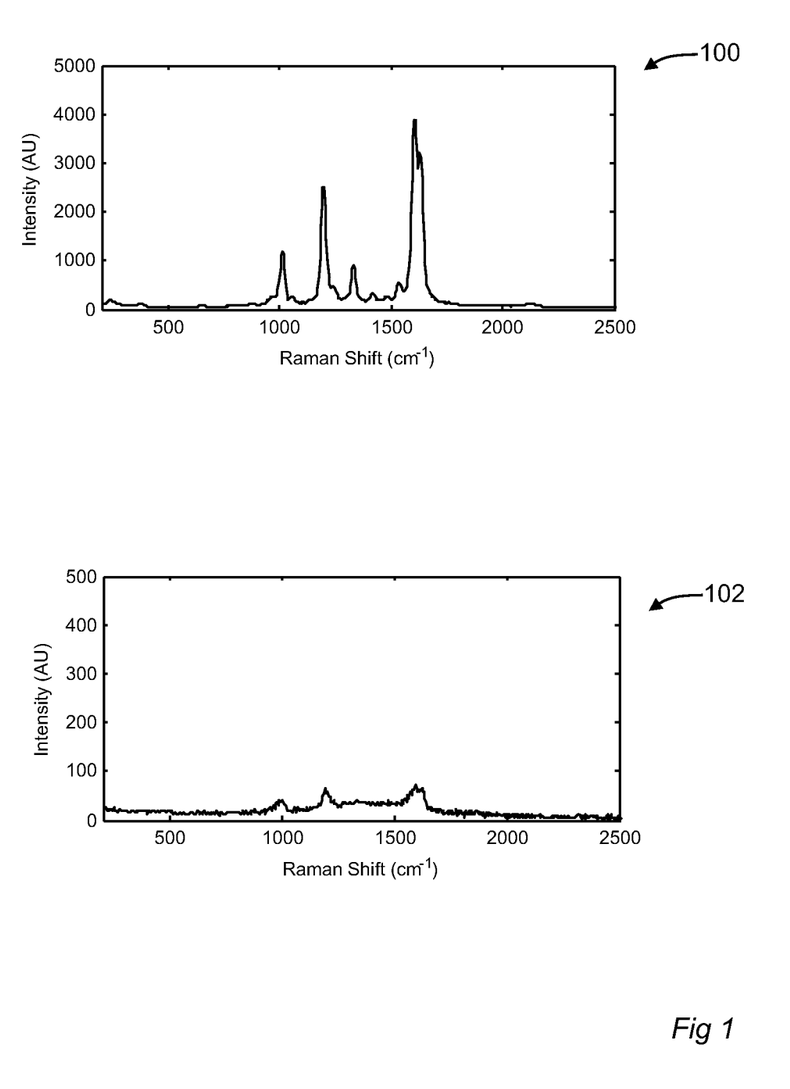
FIG. 1 is a graphic representation of the degradation in SERS signal observed with a known SERS nanotag heated for 8 minutes at 250° C.

For example, graph 100 of FIG. 1 shows the spectroscopic intensity of SERS nanotags with a selected reporter molecule upon interrogation at room temperature. Graph 102 shows the spectroscopic intensity obtained from the same SERS nanotags, after the tags were held for 8 minutes at 250° C. in an environmentally sealed thermal stage. It is clear from a comparison of graph 100 with graph 102 that elevated temperature caused substantial degradation of the signal that can be obtained from this SERS nanotag and reporter combination.

The present invention is directed toward overcoming one or more of the problems discussed above.

SUMMARY

One embodiment comprises a particle and in particular a nanoparticle. The particle comprises a surface-enhanced spectroscopy (SES) active core and a SES active reporter associated with the SES core wherein the particle produces a measurable and thermally stable SES spectrum upon optical interrogation. As used herein, thermally stable may be defined as maintaining a measurable SES spectrum after the particle or any material tagged with the particle has been exposed to a temperature substantially higher than room temperature. For example, thermally stable may be used to describe a particle able to return an SES spectrum after the particle or a material tagged with the particle has been exposed to a temperature in excess of 100° C., 200° C., 300° C., 400° C. or another elevated temperature.

The particle may be made thermally stable by selecting a thermally stable reporter molecule or through the implementation of specific particle structure. For example, the reporter may comprise a conjugated polyaromatic compound, a porphyrin compound, a phthalocyanine compound, a large network fused carbon structure, a metal oxide, an ionic liquid or similar thermally stable reporter.

The particle may include an SES-active core which may comprise a hollow shell with the reporter molecules located within the hollow shell. In hollow shell embodiments, the reporter may include but is not limited to an ionic liquid, an SES active polymer, an ion exchange resin, or a solid phase microextraction resin.

A method of manufacturing a particle is also disclosed. The method includes providing a surface enhanced spectroscopy (SES)-active core and associating an SES active reporter with the SES-active core, wherein the particle has a measurable and thermally stable SES spectrum as described above.

Also disclosed is a method of tagging a material. The tagging method comprises providing a thermally stable SES active particle as described above and associating the particle with a material of interest. The method of tagging may further include obtaining a SES spectrum from the particle in association with the material of interest after the material of interest has been heated to a temperature in excess of room temperature. For example, a material of interest and taggant particle may have been heated to a temperature of 100° C., 200° C., 300° C., 400° C. or another elevated temperature without adversely affecting the optical functionality of the taggant.

DESCRIPTION

Unless otherwise indicated, all numbers expressing quantities of ingredients, dimensions, reaction conditions and so forth used in the specification and claims are to be understood as being modified in all instances by the term "about".

In this application and the claims, the use of the singular includes the plural unless specifically stated otherwise. In addition, use of "or" means "and/or" unless stated otherwise. Moreover, the use of the term "including", as well as other forms, such as "includes" and "included", is not limiting. Also, terms such as "element" or "component" encompass both elements and components comprising one unit and elements and components that comprise more than one unit unless specifically stated otherwise.

In general, taggants are materials, substances, molecules, ions, polymers, nanoparticles, microparticles, or other matter, incorporated into, onto or otherwise associated with objects for the purposes of identification or quantitation. More specifically, taggants are used in activities and products including but not limited to detection, analysis, and/or quantification measurements related to brand security, brand protection, trademark protection, product security, product identification, brand diversion, barcoding, grey market remediation, friend-or-foe analysis, product life cycle analysis, counterfeiting, anti-counterfeiting, forensic analysis of authenticity, authentication, biometrics, object tracking, chain-of-custody analysis, product tampering, anti-smuggling, smuggling detection, supply-chain tracking, product tracking, lost revenue recovery, product serialization, serialized authentication, freshness tracking, sell-by date tracking, use-by date tracking, and standoff detection/identification.

Taggants can be added to all forms of matter, including but not limited to solids, liquids, gases, gels, foams, semi-solids, glasses, plasmas, liquid crystals, amorphous and magnetically-ordered solids, superconductors, superfluids, Bose-Einstein condensates, and supersolids.

The addition of taggants to liquids, and in particular liquid hydrocarbons such as fuel, diesel oil, gasoline, kerosene, ethanol, biodiesel, methanol, crude oil, fuel additives, etc. is recognized to be useful for a number of reasons. For example, the addition of a taggant allows protection against counterfeiting, or use of the hydrocarbon in an improper setting (i.e. brand diversion). Likewise, the ability to measure the concentration of a taggant in a hydrocarbon allows a determination of purity: if the concentration is lower than added, it suggests that the sample has been tampered with (for example by addition of a less valuable hydrocarbon). Often, this tampering can be at the level of a 1-5%, so highly accurate and precise measurements of taggants are required. Measuring taggant concentration can also be invaluable for process monitoring, where crude oil (for example) is often mixed with mud, steam, water, and other impurities, and where knowledge of the actual oil concentration impacts how selected processes are carried out. In another example, when fuel products with different owners share the same infrastructure (e.g. a pipeline), a tagged fuel allows operators to know which fuel is at which location at which time.

Likewise, addition of a taggant also provides insurance against legal liability. For example, the absence of taggant in a spilled sample of oil or gasoline allows fuel owners who have added taggant to their oil or gasoline to be exempt from liability. In many cases, the use of known taggants results in insufficient precision, detection accuracy or other problems.

In other applications, taggants may be exposed to extremes in temperature. For example, taggants are often added to flame retardant materials to insure against liability: if the taggant is not found after a fire, then a counterfeit flame retardant material was used.

In another example, high temperatures are often used to process materials, including but not limited to oils and hydrocarbons, solids, polymers, and so forth. Taggants can be used to monitor these processes, but only if they are stable at the temperatures used.

Many known methods of detecting taggants utilize one of several spectroscopic techniques, for example a surface-enhanced spectroscopy (SES) techniques such as SERS or SERRS. Broadly speaking, suitable materials fall in two categories: nano-/microscale and macroscopic. For example, certain sizes and shapes of Ag and Au nanoparticles, and aggregates thereof, are known to support SERS. Likewise, a large variety of macroscopic SERS substrates have been described in the literature, including electrodes, evaporated films, Langmuir-Blodgett films, 2-dimensional planar arrays, and so forth.

Known prior art tagging methods which utilize SERS-active tags typically include a reporter molecule or dye with known SERS-active characteristics. For example, a known SERS-active chemical can be added as a dye to mark fuel and a subsequent SERS spectrum obtained when the SERS-active dye is associated with a SERS-active metal particle or substrate. Only a limited number of SERS active chemicals are known.

Many of the embodiments disclosed herein feature the use of a surface-enhanced spectroscopy (SES) active taggant. The most widely studied have been surface-enhanced Raman scattering and surface-enhanced fluorescence (SEF). But a variety of other surface enhanced phenomena have been observed including surface-enhanced hyper Raman scattering (SEHRS), surface-enhanced hyper Raman resonance scattering (SEHRRS), surface-enhanced Rayleigh scattering, surface-enhanced second harmonic generation (SHG), surface-enhanced infrared absorption reflectance (SEIRA), and surface-enhanced laser desorption ionization (SELDI). These are part of a wider field known as plasmon enhancement or plasmon-enhanced spectroscopy, which in addition to the phenomena mentioned above includes surface plasmon enhanced emission (such as SPASERS—surface plasmon amplification of spontaneous emission of radiation), plasmon enhanced diffraction, and plasmon enhanced optical transmission. Plasmon enhancement is also a method to increase the efficiency of solar cells. As used throughout this disclosure SES includes the above listed and any related or similar spectroscopic technique.

Many of the examples herein are described with respect to SERS. It must be noted however that the methods, compositions and particles disclosed herein are equally applicable to SERRS, SEHRS, SEF, SEHRRS, SHG, SEIRA, SPASERS, or other surface enhanced or plasmon enhanced SES technique.

As noted above, one type of known SERS-active nanoparticle is a SERS nanotag, as described in U.S. Pat. Nos. 6,514,767, 6,861,263, 7,443,489 and elsewhere. All matters disclosed in U.S. Pat. Nos. 6,514,767, 6,861,263 and 7,443,489 are incorporated herein in their entirety for all matters disclosed therein. In a conventional SERS nanotag composition, a reporter molecule is adsorbed to a SERS-active surface, and both the SERS-active surface and the reporter are encapsulated, typically with silica or a glass. One advantage of a silica coating is that it prevents the adsorbed molecule from diffusing away, and also prevents other molecules from adsorbing to the surface. This imparts a level of robustness and environmental insensitivity to the SERS nanotag particles that is, for many applications, a desirable feature. As described above however, the reporter molecules used with known SERS nanotags are subject to degradation at temperatures significantly higher than room temperature, such as 250° C.

In certain circumstances it is desirable to have the characteristic SERS signature of a particle remain stable at an elevated temperature. For example, it may be useful to fabricate an embodiment of a SERS particle having a reporter, where the SERS signature remains stable even though the tagged material (a fuel for instance) is subjected to combustion. As used herein, an elevated temperature may be defined as higher than common room temperatures. Alternatively an elevated temperature may be defined as higher than 100° C. Alternatively an elevated temperature may be defined as higher than 200° C. Alternatively an elevated temperature may be defined as higher than 300° C. Alternatively an elevated temperature may be defined as higher than 400° C.

The overall stability of SERS response over temperature extremes, pressure extremes, and variable chemical environment can be a function of the reporter choice and can also be a function of taggant structure, or a combination of structure and reporter choice.

Generally, the thermal stability of a reporter molecule may be affected in two separate, but possibly complimentary ways. First, the reporter molecule may be selected to have, or modified to have, intrinsic stability at high temperatures. Second, thermal stability may be a function of the stability of the bond of the reporter to the enhancing metal surface. Thus, one method of making a thermally stable taggant is to use a reporter molecule having a structure that is known or configured to be stable at high temperatures. For example, many conjugated polyaromatic systems (either fused or not fused) are known to be stable at temperatures over 400° C. These compounds not only are stable, but also present very high Raman cross-sections. The most common fused ring molecule types are naphthalene, anthracene, phenanthrene and pyrene derivatives generally having the structure shown below. Thermal stability is even higher for perfluorinated aromatic compounds.

The replacement of some carbon atoms by nitrogen in the above and other reporter candidates may decrease stability somewhat, but the presence of nitrogen atoms is necessary for more effective binding to the enhancing metal surface of a typical taggant.

Representative reporters that would be stable at temperatures higher than 400° C. include but are not limited to pentafluoropyridine, perfluoro-4,4'-bipyridine, perfluoro-2,2'-bipyridine, perfluoro-2,7-diazapyrene, quinoline, isoquinoline, pyrimidine, pyridine, thiophene, dibenzothiophene, 2,2'-bithiophene, 1,4-di-(4-pyridyl)benzene, 1,3,5-tri-(4-pyridyl)benzene, 4-phenylquinoline, 6-phenylquinoline, 6-(4-pyridyl)isoquinoline, 1,10-phenanthroline, 1,7-phenanthroline, 4,7-phenanthroline, 3,8-phenanthroline, 1-azapyrene, 2-azapyrene, 2,7-diazapyrene, 1,8-naphthyridine, 1,6-naphthyridine, 1,5-naphthyridine, 2-azaanthracene, 2,7-diazaanthracene, benzothiazole, benzoxazole, 4-phenylpyridine, 2-phenylpyridine, 4-(4-pyridyl)imidazole, 4 phenylimidazole and 4-(4-pyridyl)biphenyl.

An alternative variety of thermally stable reporters are the porphyrin and phthalocyanine family of compounds having structure as generally illustrated below.

Porphyrin

Phthalocyanine

These structures contain bonds that are somewhat labile, but the decomposition products are not volatile and are stable enough to regenerate the original bonds once the external thermal stimulus recedes. There are a number of commercial derivatives of these structural families, and well established synthetic procedures exist which can give rise to a large variety of compounds in this family which are suitable for use as thermally stable reporters, including thiolated derivatives.

Examples of commercially available porphyrins and phthalocyanines containing functional groups facilitating attachment to an enhancing metal surface are shown below. Other derivatives with alternative modes of attachment can be synthesized.

4,4',4'',4'''-tetraaza-29H,31H-phthalocyanine 5,10,15,20-Tetra(4-pyridyl)-21H,23H-porphine Alternatively, carbon nanotubes and fullerene structures (i.e. $C_{60}$ and $C_{70}$ derivatives) may be used as thermally stable reporters. The very large network of fused aromatic rings present in these structures can give rise to high Raman cross-sections, and these molecules are known to be stable at high temperatures. Carboxylated and hydroxylated fullurenes are presently commercially available. These compounds can be used as reporters as well as precursors to synthesize pyridyl or thiol containing fullerenes.

The thermal stability of a reporter molecule may also be affected by the stability of the bond of the reporter to the enhancing metal surface at elevated temperature. The stability of a reporter to metal bond at high temperatures may be enhanced by the use of reporters that have two or more binding groups, for example, pyridyl and/or thiol groups. The higher the binding order, the more stable the reporter-metal system is likely to be. Multiple binding groups may be located on the same side of the reporter molecule to bind to the same metal surface, or may be located on opposite sides of the molecule to bind to two different particles.

Metal oxides, and mixed metal oxides are another class of useful reporters for thermally stable SERS nanotags. Multiple types of oxide-based reporters are possible. For example, a metal nanoparticle core can be coated with a metal oxide that is thermally stable. Alternatively, a SERS nanotag can be prepared with a non-oxide material that converts to a metal oxide at elevated temperatures. In a third scenario, the oxide exhibits a temperature dependent Raman spectrum. For example, as described in *Inorganic Chemistry*, Vol. 48, No. 3, 2009, pp. 946-952, nanostructured lithium metal phosphates $LiMPO_4$ (M) Mn, Fe, Co, and Ni) can be prepared by reactions of precursors at temperatures as low as 300° C. $CaCu_3Ti_4O_{12}$ (CCTO) is an example of a metal oxide with very high dielectric constants. These materials exhibit intense Raman spectra. For example, CCTO has four bands between 200 and 700 cm-1 (see Phys. Rev. B 66, 132102 (2002).

Antimony oxides and oxyfluorides are used as flame and thermal resistant materials and consequently have high thermal stability. The Raman spectra of a series of Sb (III) oxides and oxyfluorides have been measured (Journal of Structural Chemistry. Vol. 50, No. 1, pp. 60-66, 2009). These species exhibit a large series of Raman bands from 100 to 700 $cm^{-1}$.

A suitable method for the preparation of SERS nanotags with oxides or mixed metal oxides as reporters is to incorporate preformed oxides, or oxide precursors as described above, into thermally unstable polymer films. Subsequently, heat may be used to decompose and eliminate the polymers. For example, a SERS-active particle could be coated with thermally depolymerizable tertiary polycarbonates. These polymers degrade when heated at around 200° C. The ultimate degradation temperature depends upon polymer structure. Degradation of these polymers results in only volatile compounds as products, leaving no solid residue (*Macromolecules*, 1986, 19 (1), pp 13-19). Oxide particles could be associated with the polymer film using electrostatic or other means. Thereafter, elevated temperatures may lead to decomposition and loss of the organic film, bringing the oxide into proximity with the metal nanoparticle surface. Alternatively, oxides can be synthesized directly onto metal nanoparticle by solvothermal or precipitation methods.

Suitable SERS reporters that are stable at elevated temperatures may also be formed by applying an external stimulus to an already finished tag. In this way a generally inactive tag can be switched on by high temperature and remain active in use when subjected to high temperature. For example, a polymer containing pendant Ruthenium complexes and a third ligand may be attached to the surface of a metal particle. The polymer coated particles may then be coated with 20-30 nm of silica. This step results in the polymer and ligand locked in close proximity to the metal surface. Reaction between Ru and the ligand does not occur at room temperature, but upon heating these constituents react to form a trisdipyridyl Ru complex, which contains functional groups to attach to the metal surface (ethynyl) and which are SERS active, as shown below. The reaction does not need to proceed to completion since just a portion of the complexes must to be present to have measurable SERS.

An alternative approach to the activation of SERS tags with heat is based upon the representative reaction shown below. An initial compound may be absorbed to the enhancing metal core. The absorbed organic molecule on the gold or other SERS enhancing metal surface may be locked in place by performing a silica coating of the particle. Upon heating, the reporter molecule breaks up and releases ethylene, forming a new aromatic ring that extends the conjugation of the molecule, increases its Raman cross-section and which shows a SERS spectrum.

Ionic liquids are another class of compounds that may be useful as reporters in thermally stable SERS tags. To date, ionic liquids have not been used as SERS reporters. A common class of ionic compounds contains an imidazolium cation as one of its components. This cation should generate a reasonable SERS spectrum. Since suitable ionic liquids are not as easily degraded by heat as organic compounds, depositing a room temperature ionic liquid in the interior of a hollow particle or otherwise associating an ionic liquid with an enhancing surface may result in a thermally stable tag.

Representative ionic liquids which may be used as reporters include, but are not limited to: 1-Ethyl-3-methylimidazolium chloride, 1-Ethyl-3-methylimidazolium chloride, 1-Ethyl-3-methylimidazolium methanesulfonate, 1-Butyl-3-methylimidazolium chloride, 1-Butyl-3-methylimidazolium methanesulfonate, 1-Ethyl-2,3-di-methylimidazolium ethylsulfate, 1-Ethyl-3-methylimidazolium hydrogensulfate, 1-Ethyl-3-methylimidazolium tetrachloroaluminate, 1-Butyl-3-methylimidazolium hydrogensulfate, 1-Butyl-3-methylimidazolium tetrachloroaluminate, 1-Ethyl-3-methylimidazolium acetate, 1-Butyl-3-methylimidazolium acetate, 1-Ethyl-3-methylimidazolium ethylsulfate, 1-Butyl-3-methylimidazolium methylsulfate, 1-Ethyl-3-methylimidazolium thiocyanate, 1-Butyl-3-methylimidazolium thiocyanate, 1-Ethyl-3-methylimidazolium bis(trifluoromethanesulfonyl)imide, 1-Butyl-3-methylimidazolium, bis(trifluoromethanesulfonyl)imide, 1-Ethyl-3-methylimidazolium chloride, 1-Ethyl-3-methylimidazolium chloride, 1-Ethyl-3-methylimidazolium methanesulfonate, 1-Butyl-3-methylimidazolium chloride, 1-Butyl-3-methylimidazolium methanesulfonate, 1-Ethyl-2,3-di-methylimidazolium ethylsulfate, 1-Ethyl-3-methylimidazolium hydrogensulfate, 1-Ethyl-3-methylimidazolium tetrachloroaluminate, 1-Butyl-3-methylimidazolium hydrogensulfate, 1-Butyl-3-methylimidazolium tetrachloroaluminate, 1-Ethyl-3-methylimidazolium acetate, 1-Butyl-3-methylimidazolium acetate, 1-Ethyl-3-methylimidazolium ethylsulfate, 1-Butyl-3-methylimidazolium methylsulfate, 1-Ethyl-3-methylimidazolium thiocyanate, 1-Butyl-3-methylimidazolium thiocyanate, 1-Ethyl-3-methylimidazolium bis(trifluoromethanesulfonyl)imide, and 1-Butyl-3-methylimidazolium bis(trifluoromethanesulfonyl)imide.

As described herein, an ionic liquid or other liquid reporter may be associated or contained within the hollow metal core of a particle. Hollow spherical particles or hollow particles of another shape may be made following a growth template-shell approach as described below.

As described above, the overall stability of the SERS response of a SERS active taggant particle over temperature extremes, pressure extremes, and variable chemical environment can be a function of the reporter choice, a function of taggant structure, or a combination of structure and reporter choice. For example, various types of hollow particles that feature a hollow Raman enhancing core can be made more thermally stable if the reporter is located within the core itself as described above with regard to ionic reporters. Location of the reporter within the enhancing core can limit the likelihood that an otherwise heat-sensitive reporter will diffuse away from the enhancing surface under elevated temperature.

Figure 2:
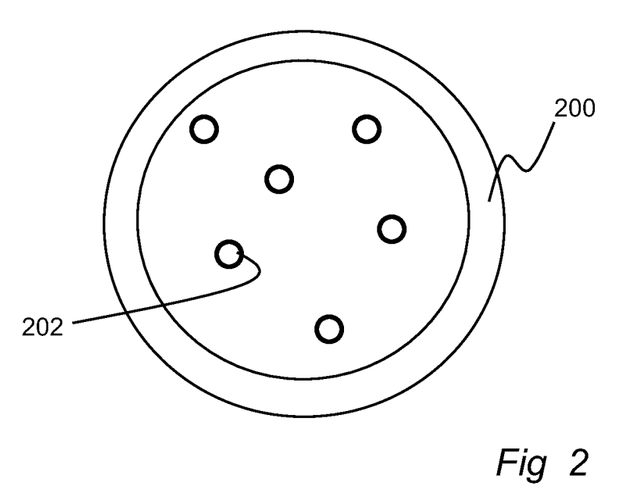
FIG. 2 is a schematic diagram of particle featuring reporter molecules within a hollow metal shell.

Hollow particles of various shapes may be made by following a growth template-shell approach. The growth template may be non-metallic (polystyrene, silica, etc.) in which case the often metal shell is added to the exterior by a seeded growth mechanism. First small seed colloids (often Au) are attached to the exterior of a silica or polymer bead. Additional Au is then grown resulting in a continuous shell. Because the shell can be prepared with some pores, the growth template is then readily removed by dissolving the growth template with the appropriate chemical. For example, Tam et al. have prepared relatively large hollow particles with plasmon resonances at 1900 nm. *Mesoscopic nanoshells: Geometry-dependent plasmon resonances beyond the quasistatic limit*, Felicia Tam, Allen L. Chen, Janardan Kundu and Hui Wang, Naomi J. Halas J. Chem. Phys. 127, 204703, 2007. Alternatively, if a Ag particle is used as the growth template, galvanic displacement of the Ag by Au has been used to prepared both hollow spheres and hollow cubes. A major advantage of core-shell nanoparticles is that the growth template may be selectively removed. $SiO_2$ growth-template cores can be removed with HF etching, and the subsequent void replaced with reporter molecule or other lower density materials to enhance the ability of these particles to remain suspended in a liquid matrix. Use of mixed Au/Ag shells (or other alloys) also allows the preparation of perforated shells by selective Ag etching, facilitating template removal/replacement. Likewise, the formation of Au nanoparticles has been demonstrated on the inner surface of an otherwise hollow silica shell, which may be followed by insertion of Raman-active materials. It is possible to expand on this method, and allow large excesses of reporter to diffuse within the shell, followed by further metal growth to seal the reporter inside. As shown in FIG. 2, once a hollow shell 200 is prepared, reporter molecules 202 may be inserted into the interior of the particle, followed by a reaction to seal the interior.

Figure 3:
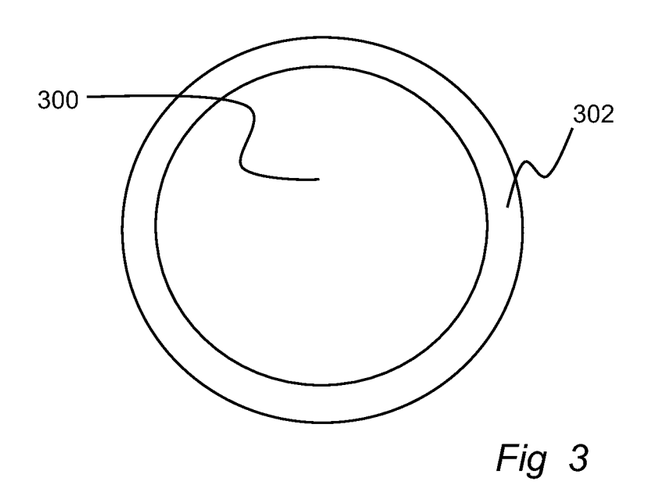
FIG. 3 is a schematic diagram of a particle featuring a SERS active polymer core surrounded by a metal shell.

Alternatively, as shown in FIG. 3, a SERS active particle could be formed with a solid, thermally stable SERS active core 300 surrounded by an enhancing metal shell 302. The core 300 could be but is not limited to a thermally stable, SERS active polymer upon which a SERS enhancing metal shell 302 has been grown or applied, alternatively, the core 300 could be a thermally stable ion exchange resin or a thermally stable solid phase microextraction resin (SPME) providing the particle with the ability to bind a SERS active reporter molecule to the core. Both a hollow particle with a SERS active reporter on the inside or a solid particle such as the core/shell particle of FIG. 3, having the enhancing surface of the outside provide for simpler particle functionalization on exterior surfaces because the chemical nature and stability of the reporter is not of concern.

A method of manufacturing a particle is also disclosed. The method includes providing a surface enhanced spectroscopy (SES)-active core and associating an SES active reporter with the SES-active core, wherein the particle has a measurable and thermally stable SES spectrum as described above.

Also disclosed is a method of tagging a material. The tagging method comprises providing a thermally stable SES active particle as described above and associating the particle with a material of interest. The method of tagging may further include obtaining a SES spectrum from the particle in association with the material of interest after the material of interest has been heated to a temperature in excess of room temperature. For example, a material of interest and taggant particle may have been heated to a temperature of 100° C., 200° C., 300° C., 400° C. or another elevated temperature without adversely affecting the optical functionality of the taggant.

The small, robust, non-toxic, and easily-attachable nature of the thermally stable particles disclosed herein allows their use for tagging virtually any desired object. The tracked object can be made of solid, liquid, or gas phase material or any combination of phases. The material can be a discrete solid object, such as a container, pill, or piece of jewelry, or a continuous or granular material, such as paint, ink, fuel, or extended piece of, e.g., textile, paper, or plastic, in which case the particles are typically distributed throughout the material.

Examples of specific materials or objects that can be tagged with the thermally stable particles disclosed herein, or into which the thermally stable particles can be incorporated include, but are not limited to:

Packaging, including adhesives, paper, plastics, labels, and seals
Agrochemicals, seeds, and crops
Artwork
Computer chips
Cosmetics and perfumes
Compact disks (CDs), digital video disks (DVDs), and videotapes
Documents, money, and other paper products (e.g., labels, passports, stock certificates)
Inks, paints, varnishes, lacquers, overcoats, topcoats, and dyes
Electronic devices
Explosives and weapons
Food and beverages, tobacco
Textiles, clothing, footwear, designer products, and apparel labels
Polymers
Insects, birds, reptiles, and mammals
Powders
Luxury goods
Other anti-counterfeiting substances or materials, such as holograms, optically variable devices, color-shifting inks, threads, and optically-active particles
Hazardous waste
Movie props and memorabilia, sports memorabilia and apparel
Manufacturing parts, automobile parts, aircraft parts, truck parts
Petroleum, fuel, lubricants, gasoline, crude oil, diesel fuel, fuel additive packages, crude oil
Pharmaceuticals, prescription drugs, over-the-counter medicines, and vaccines The thermally stable particles disclosed herein can be associated with the material in any way that maintains their association, at least until the particles are read. Depending upon the material to be tagged, the particles can be incorporated during production or associated with a finished product. Because they are so small, the particles are unlikely to have a detrimental effect on either the manufacturing process or the finished product. The particles can be associated with or attached to the material via any chemical or physical means that does not inherently interfere with particle functionality. For example, particles can be mixed with and distributed throughout a liquid-based substance such as paint, oil, or ink and then applied to a surface. They can be wound within fibers of a textile, paper, or other fibrous or woven product, or trapped between layers of a multi-layer label. The particles can be incorporated during production of a polymeric or slurried material and bound during polymerization or drying of the material. Additionally, the surfaces of the particles can be chemically derivatized with functional groups of any desired characteristic, for covalent or non-covalent attachment to the material. When the particles are applied to a finished product, they can be applied manually by, e.g., a pipette, or automatically by a pipette, spray nozzle, or the like. Particles can be applied in solution in a suitable solvent (e.g., ethanol), which then evaporates.

The thermally stable particles disclosed herein have a number of inherent properties that are advantageous for tagging and tracking applications. They offer a very large number of possible codes. For example, if a panel of particles is constructed with 20 distinguishable Raman spectra, and an object is labeled with two particles, there are 20*19/2=190 different codes. If the number of particles per object is increased to 5, there are 15,504 possible codes. Ten particles per object yields $1.1 \times 10^6$ different codes. A more sophisticated monochromator increases the number of distinguishable spectra to, e.g., 50, greatly increasing the number of possible codes. Alternatively, different amounts of thermally stable particles can be used to generate an exponentially-increased number of possible codes. For example, with just four different particle types (N=4), present at three different intensity levels (e.g. High, Medium, Low) (L=3), chosen three at a time (P=3), can generate 58 different codes. With N=10, P=3, L=1, the number of codes is 175. With N=50, P=5, L=4, over a billion codes are possible.

In some embodiments, the particles may be applied to a document or other item in an ink or other marking material. Inks include, but are not limited to flexographic ink, lithographic ink, silkscreen ink, gravure ink, bleeding ink, coin reactive ink, erasable ink, pen reactive ink, heat reactive ink, visible infrared ink, optically variable ink, and penetrating ink, photochromic ink, solvent/chemical reactive ink, thermochromic ink, and water fugitive ink. A PSP may also be applied in electrophotographic and ink jet printing machines and other systems including offset lithography, letterpress, gravure, heliogravure, xerography, photography, silk-screening systems, systems for imagewise deposition of discrete quantities of a marking material on a substrate surface, such as paint, chemical, and film deposition systems; and systems for integration of colorant materials in an exposed surface of a fibrous substrate, such as textile printing systems.

It should be noted that additional security features may be included or utilized along with the disclosed tags for a particular item or documents. One such additional security feature may be a separate security ink, such as bleeding ink, coin reactive ink, erasable ink, pen reactive ink, heat reactive ink, visible infrared ink, optically variable ink, penetrating ink, photochromic ink, solvent/chemical reactive ink, thermochromic ink or water fugitive ink. The tags may be applied as part of the ink, or in a separate step. Other non-ink based security features which may be utilized in addition to the disclosed tags for document or item marking include the use of an ascending serial number (horizontal and/or vertical format), bar code and numerals, colored fibers, embedded security thread, face-back optical registration design (transparent register), foil imprints, holograms, latent impressions, micro printing, optical variable devices (OVD), planchettes, raised marks, segmented security threads, and watermarks.

The disclosed particles may be applied by coating an image, including but not limited to a hologram image, made with toner or ink compositions known in the art, as with an overcoat varnish, or a starch overcoat.

In the case of documents with other security features, such as those including polymer threads or metal foils, the particles may be applied to additional feature, such as the thread or the foil. Single tags may be considered to represent a bit of data that may be changeable according to the methods described herein. Thus groups of distinguishable thermally stable particles disclosed herein may be applied to constitute an "alphabet" and combined as words or encoded information, which may be selectively variable, or variable over time.

The thermally stable particles disclosed herein can be identified using a conventional spectrometer, for example a Raman spectrometer. In fact, one benefit of using SERS particles is the versatility of excitation sources and detection instrumentation that can be employed for Raman spectroscopy. Visible or near-IR lasers of varying sizes and configurations can be used to generate Raman spectra. Portable, handheld, and briefcase-sized instruments are commonplace. At the same time, more sophisticated monochromators with greater spectral resolving power allow an increase in the number of unique taggants that can be employed within a given spectral region. For example, the capability to distinguish between two Raman peaks whose maxima differ by only 3 cm$^{-1}$ is routine.

Typically, if a suitable waveguide (e.g., optical fiber) is provided for transmitting light to and from the object, the excitation source and detector can be physically remote from the object being verified. This allows the disclosed particles to be used in locations in which it is difficult to place conventional light sources or detectors. The nature of Raman scattering and laser-based monochromatic excitation is such that it is not necessary to place the excitation source in close proximity to the Raman-active species. Moreover, the thermally stable particles disclosed herein are amenable for use with all known forms of Raman spectrometers, including some more recent implementations, including spatially offset Raman, Raman absorption spectrometers, instruments to measure Raman optical activity, and so forth.

Another characteristic of thermally stable particles is that the measurement of their spectra does not need to be strictly confined to "line of sight" detection, as with, e.g., fluorescent tags. Thus their spectrum can be acquired without removing the particles from the tagged object, provided that the material is partially transparent to both the excitation wavelength and the Raman photon. For example, water has negligible Raman activity and does not absorb visible radiation, allowing the particles disclosed herein in water to be detected. The thermally stable particles can also be detected when embedded in, e.g., clear plastic, paper, or certain inks.

The disclosed particles also allow for quantitative verification, because the signal intensity is an approximately linear function of the number of analyte molecules. For standardized particles (uniform analyte distribution), the measured signal intensity reflects the number or density of particles. If the particles are added at a known concentration, the measured signal intensity can be used to detect undesired dilution of liquid or granular materials.

Various embodiments of the disclosure could also include permutations of the various elements recited in the claims as if each dependent claim was a multiple dependent claim incorporating the limitations of each of the preceding dependent claims as well as the independent claims. Such permutations are expressly within the scope of this disclosure.

While the embodiments disclosed herein have been particularly shown and described with reference to a number of examples, it would be understood by those skilled in the art that changes in the form and details may be made to the various embodiments disclosed herein without departing from the spirit and scope of the disclosure and that the various embodiments disclosed herein are not intended to act as limitations on the scope of the claims.

All references sited herein are incorporated in their entirety by reference for all matters disclosed therein.

What is claimed is:

1. A particle comprising:
    a surface-enhanced spectroscopy (SES)-active metal core; and
    a SES-active reporter associated with said SES-active metal core, wherein said SES-active reporter comprises a conjugated polyaromatic system modified to have one or more carbon atoms replaced with one or more nitrogen atoms, wherein said particle has a measurable and thermally stable SES spectrum after being heated to a temperature of 200° C.

2. The particle of claim 1 wherein the conjugated polyaromatic system comprises at least one of the following before being modified to have one or more carbon atoms replaced with one or more nitrogen atoms: pentafluoropyridine, perfluoro-4,4'-bipyridine, perfluoro-2,2'-bipyridine, perfluoro-2,7-diazapyrene, quinoline, isoquinoline, pyrimidine, pyridine, thiophene, dibenzothiophene, 2,2'-bithiophene, 1,4-di-(4-pyridyl) benzene, 1,3,5-tri-(4-pyridyl)benzene, 4-phenylquinoline, 6-phenylquinoline, 6-(4-pyridyl)isoquinoline, 1,10-phenanthroline, 1,7-phenanthroline, 4,7-phenanthroline, 3,8-phenanthroline, 1-azapyrene, 2-azapyrene, 2,7-diazapyrene, 1,8-naphthyridine, 1,6-naphthyridine, 1,5-naphthyridine, 2-azaanthracene, 2,7-diazaanthracene, benzothiazole, benzoxazole, 4-phenylpyridine, 2-phenylpyridine, 4-(4-pyridyl)imidazole, 4 phenylimidazole and 4-(4-pyridyl)biphenyl.

3. The particle of claim 1 wherein the SES-active reporter comprises at least one of a porphyrin and phthalocyanine compound before being modified to have one or more carbon atoms replaced with one or more nitrogen atoms.

4. The particle of claim 1 wherein the SES-active reporter comprises a large network fused carbon structure before being modified to have one or more carbon atoms replaced with one or more nitrogen atoms.

5. The particle of claim 1 wherein the SES-active metal core comprises a hollow shell and the SES-active reporter is located within the hollow shell.

6. The particle of claim 1 wherein the particle has a measurable and thermally stable SES spectrum after being heated to a temperature of 300° C.

7. The particle of claim 1 wherein the particle has a measurable and thermally stable SES spectrum after being heated to a temperature of 400° C.

8. A method of manufacturing a particle comprising:
providing a surface-enhanced spectroscopy (SES)-active metal core;
providing a conjugated polyaromatic system molecule;
modifying the conjugated polyaromatic system molecule by replacing one or more carbon atoms with one or more nitrogen atoms to create a SES-active reporter; and
associating a SES-active reporter with said SES-active metal core, wherein said particle has a measurable and thermally stable SES spectrum after being heated to a temperature of 200° C.

9. The method of manufacturing a particle of claim 8 wherein the conjugated polyaromatic system comprises at least one of a porphyrin and phthalocyanine compound before being modified to have one or more carbon atoms replaced with one or more nitrogen atoms.

10. The method of manufacturing a particle of claim 8 wherein conjugated polyaromatic system comprises a large network fused carbon structure before being modified to have one or more carbon atoms replaced with one or more nitrogen atoms.

11. The method of manufacturing a particle of claim 8 wherein the SES-active metal core comprises a hollow shell and the SES-active reporter is located within the hollow shell.

12. The method of manufacturing a particle of claim 8 wherein the particle has a measurable and thermally stable SES spectrum after being heated to a temperature of 300° C.

13. The method of manufacturing a particle of claim 8 wherein the particle has a measurable and thermally stable SES spectrum after being heated to a temperature of 400° C.

14. The method of claim 8 wherein the conjugated polyaromatic system comprises at least one of the following before being modified to have one or more carbon atoms replaced with one or more nitrogen atoms: pentafluoropyridine, perfluoro-4,4'-bipyridine, perfluoro-2,2'-bipyridine, perfluoro-2,7-diazapyrene, quinoline, isoquinoline, pyrimidine, pyridine, thiophene, dibenzothiophene, 2,2'-bithiophene, 1,4-di-(4-pyridyl) benzene, 1,3,5-tri-(4-pyridyl)benzene, 4-phenylquinoline, 6-phenylquinoline, 6-(4-pyridyl)isoquinoline, 1,10-phenanthroline, 1,7-phenanthroline, 4,7-phenanthroline, 3,8-phenanthroline, 1-azapyrene, 2-azapyrene, 2,7-diazapyrene, 1,8-naphthyridine, 1,6-naphthyridine, 1,5-naphthyridine, 2-azaanthracene, 2,7-diazaanthracene, benzothiazole, benzoxazole, 4-phenylpyridine, 2-phenylpyridine, 4-(4-pyridyl)imidazole, 4 phenylimidazole and 4-(4-pyridyl)biphenyl.

15. A method of tagging a material comprising:
providing a particle comprising a surface-enhanced spectroscopy (SES)-active metal core and a SES-active reporter associated with said SES-active metal core, wherein said SES-active reporter comprises a conjugated polyaromatic system modified to have one or more carbon atoms replaced with one or more nitrogen atoms, wherein said particle has a measurable and thermally stable SES spectrum; and
associating the particle with a material of interest; and
obtaining a SES spectrum from the particle in association with the material of interest after the material of interest has been heated to a temperature of 200° C.

16. The method of tagging a material of claim 15 further comprising obtaining a SES spectrum from the particle in association with the material of interest after the material of interest has been heated to a temperature of 300° C.

17. The method of tagging a material of claim 15 further comprising obtaining a SES spectrum from the particle in association with the material of interest after the material of interest has been heated to a temperature of 400° C.

18. The method of claim 15 wherein the conjugated polyaromatic system comprises at least one of the following before being modified to have one or more carbon atoms replaced with one or more nitrogen atoms: pentafluoropyridine, perfluoro-4,4'-bipyridine, perfluoro-2,2'-bipyridine, perfluoro-2,7-diazapyrene, quinoline, isoquinoline, pyrimidine, pyridine, thiophene, dibenzothiophene, 2,2'-bithiophene, 1,4-di-(4-pyridyl) benzene, 1,3,5-tri-(4-pyridyl) benzene, 4-phenylquinoline, 6-phenylquinoline, 6-(4-pyridyl)isoquinoline, 1,10-phenanthroline, 1,7-phenanthroline, 4,7-phenanthroline, 3,8-phenanthroline, 1-azapyrene, 2-azapyrene, 2,7-diazapyrene, 1,8-naphthyridine, 1,6-naphthyridine, 1,5-naphthyridine, 2-azaanthracene, 2,7-diazaanthracene, benzothiazole, benzoxazole, 4-phenylpyridine, 2-phenylpyridine, 4-(4-pyridyl)imidazole, 4 phenylimidazole and 4-(4-pyridyl)biphenyl.

* * * * *